(12) United States Patent
Kuzmin et al.

(10) Patent No.: US 11,262,309 B2
(45) Date of Patent: Mar. 1, 2022

(54) METHODS FOR LIPID MEASUREMENT IN CELLS

(71) Applicants: Advanced Cytometry Instrumentation Systems, LLC, Buffalo, NY (US); The Research Foundation for The State University of New York, Amherst, NY (US)

(72) Inventors: Andrey N. Kuzmin, East Amherst, NY (US); Artem Pliss, Amherst, NY (US); Paras N. Prasad, East Amherst, NY (US)

(73) Assignees: Advanced Cytometry Instrumentation Systems, LLC, Buffalo, NY (US); The Research Foundation for The State University of New York, Amherst, NY (US)

( * ) Notice: Subject to any disclaimer, the term of this patent is extended or adjusted under 35 U.S.C. 154(b) by 0 days.

(21) Appl. No.: 16/509,372

(22) Filed: Jul. 11, 2019

(65) Prior Publication Data

US 2020/0018706 A1 Jan. 16, 2020

Related U.S. Application Data

(60) Provisional application No. 62/696,656, filed on Jul. 11, 2018.

(51) Int. Cl.
*G01N 21/65* (2006.01)
*G01N 33/50* (2006.01)
(Continued)

(52) U.S. Cl.
CPC ............... *G01N 21/65* (2013.01); *G01J 3/44* (2013.01); *G01N 33/5076* (2013.01); *G01N 33/92* (2013.01)

(58) Field of Classification Search
CPC .... G01N 21/65; G01N 33/5076; G01N 33/92; G01N 21/658; G01N 2021/656;
(Continued)

(56) References Cited

U.S. PATENT DOCUMENTS 5,106,387 A * 4/1992 Kittrell ............... A61B 1/00096
600/477
5,125,404 A * 6/1992 Kittrell ................ A61B 5/0075
600/342

(Continued)

OTHER PUBLICATIONS

Kuzmin et al, Resonance Raman Probes for Organelle-Specific Labeling in Live Cells, Nature Sc. Reports, (2016).*

(Continued)

*Primary Examiner* — Mohamed K Amara
(74) *Attorney, Agent, or Firm* — Hodgson Russ LLP

(57) ABSTRACT

Methods for determining lipid composition. The lipid(s) in a composition may include phospholipids. A method may be carried out on an individual cell. A method may compare the Raman spectrum of the portion of a cell with a model Raman spectrum, which does not include the lipid component, where the difference between the Raman spectrum of the portion of the cell and the model Raman spectrum correlates to the lipid composition in the portion of the cell in the portion of the cell). A method may be used to diagnose a disease such as, for example, cancers, including breast cancer, prostate cancer, and via the presence and/or absence of abnormal or damaged cells in an individual.

20 Claims, 11 Drawing Sheets
(6 of 11 Drawing Sheet(s) Filed in Color)

(51) Int. Cl.
  *G01J 3/44* (2006.01)
  *G01N 33/92* (2006.01)

(58) Field of Classification Search
  CPC ......... G01N 2405/04; G01N 2021/653; G01N 2405/00; G01N 2570/00; G01N 2333/775; G01N 2405/08; G01N 2500/10; G01N 2021/655; G01N 33/56911; G01J 3/44; G01J 2003/4424; A61B 5/1455; A61K 2300/00; A61K 45/06
  See application file for complete search history.

(56) References Cited

U.S. PATENT DOCUMENTS

| | | | | |
|---|---|---|---|---|
| 5,304,173 | A * | 4/1994 | Kittrell | A61B 1/00096 600/477 |
| 5,348,003 | A * | 9/1994 | Caro | A61B 5/14546 356/39 |
| 5,419,323 | A * | 5/1995 | Kittrell | A61B 5/0071 600/476 |
| 5,733,739 | A * | 3/1998 | Zakim | G01N 21/359 435/29 |
| 5,991,653 | A * | 11/1999 | Richards-Kortum | A61B 5/0059 250/339.01 |
| 6,108,081 | A * | 8/2000 | Holtom | G01J 3/44 356/301 |
| 6,642,012 | B1 * | 11/2003 | Ashdown | G01N 21/35 435/7.24 |
| 6,833,542 | B2 * | 12/2004 | Wang | B07C 5/34 250/251 |
| 7,619,105 | B2 * | 11/2009 | Green | A01H 5/10 435/190 |
| 8,253,936 | B2 * | 8/2012 | Cohen | G01J 3/44 356/301 |
| 8,326,404 | B2 * | 12/2012 | Zeng | A61B 5/0071 600/475 |
| 8,416,405 | B2 * | 4/2013 | Panza | G01J 3/44 356/301 |
| 10,365,220 | B2 * | 7/2019 | Chan | G01N 21/65 |
| 10,716,613 | B2 * | 7/2020 | Mueller | A61B 5/0084 |
| 10,722,292 | B2 * | 7/2020 | Arya | A61B 18/1445 |
| 2003/0191398 | A1 * | 10/2003 | Motz | A61B 5/4312 600/478 |
| 2004/0012778 | A1 * | 1/2004 | Li | G01J 3/44 356/301 |
| 2004/0063216 | A1 * | 4/2004 | Lubocki | A61B 5/0059 436/173 |
| 2004/0073120 | A1 * | 4/2004 | Motz | A61B 5/0086 600/478 |
| 2004/0135997 | A1 * | 7/2004 | Chan | C12Q 1/6825 356/301 |
| 2005/0048581 | A1 * | 3/2005 | Chiu | B82Y 30/00 435/7.1 |
| 2005/0069900 | A1 * | 3/2005 | Lentrichia | G01N 33/54366 435/6.18 |
| 2005/0084980 | A1 * | 4/2005 | Koo | G01J 3/44 436/171 |
| 2005/0123563 | A1 * | 6/2005 | Doranz | A61K 47/6901 424/204.1 |
| 2005/0244336 | A1 * | 11/2005 | Low | A61K 49/006 424/9.6 |
| 2006/0054506 | A1 * | 3/2006 | Natan | G01N 21/658 205/112 |
| 2006/0281068 | A1 * | 12/2006 | Maier | G01N 21/65 435/4 |
| 2009/0317802 | A1 * | 12/2009 | Bhatia | B82Y 15/00 435/6.11 |
| 2010/0241357 | A1 * | 9/2010 | Chan | G01J 3/44 702/19 |
| 2011/0027910 | A1 * | 2/2011 | Weir | C07K 14/705 436/501 |
| 2011/0176130 | A1 * | 7/2011 | Gu | G02B 6/02385 356/301 |
| 2012/0085900 | A1 * | 4/2012 | Verbeck, IV | G01N 21/65 250/282 |
| 2012/0294869 | A1 * | 11/2012 | Pizzorno | A23L 33/10 424/158.1 |
| 2013/0045947 | A1 * | 2/2013 | Xu | G01N 33/57411 514/58 |
| 2013/0273561 | A1 * | 10/2013 | Walker | G01N 33/54373 435/7.2 |
| 2014/0296089 | A1 * | 10/2014 | Holmes | B01L 9/06 506/9 |
| 2016/0054343 | A1 * | 2/2016 | Holmes | G01N 21/75 506/2 |
| 2016/0178439 | A1 * | 6/2016 | Freudiger | G01N 15/1434 356/301 |
| 2016/0243261 | A1 * | 8/2016 | Min | G01N 33/583 |
| 2016/0310572 | A1 * | 10/2016 | Yu | A61K 38/1841 |
| 2017/0023482 | A1 * | 1/2017 | Cicerone | G02B 21/365 |
| 2017/0191049 | A1 * | 7/2017 | Samli | C07K 1/14 |
| 2017/0281570 | A1 * | 10/2017 | Gurtner | A61K 47/26 |
| 2018/0149597 | A1 * | 5/2018 | Umezaki | G01N 21/65 |
| 2019/0125829 | A1 * | 5/2019 | Pajvani | A61P 9/10 |
| 2019/0187048 | A1 * | 6/2019 | Wood | C12Q 1/04 |
| 2019/0360933 | A1 * | 11/2019 | Singamaneni | G01N 21/554 |
| 2020/0376022 | A1 * | 12/2020 | Domenyuk | C12Q 1/6886 |

OTHER PUBLICATIONS

Levchenko et al, Macromolecular Profiling of Organelles in Normal Diploid and Cancer Cells, Ana. Chem (2017).*

* cited by examiner

METHODS FOR LIPID MEASUREMENT IN CELLS

CROSS REFERENCE TO RELATED APPLICATIONS

This application claims priority to U.S. Provisional Application No. 62/696,656, filed on Jul. 11, 2018, the disclosure of which is hereby incorporated by reference.

STATEMENT REGARDING FEDERALLY SPONSORED RESEARCH OR DEVELOPMENT

This invention was made with government support under contract no. GM116193-02 awarded by the National Institutes of Health (National Institute of General Medical Sciences). The government has certain rights in the invention.

BACKGROUND OF THE DISCLOSURE

Previous reviews emphasize the role of lipid synthesis in cancer metabolism and tumor development. Although fatty acid (FA) and cholesterol biosyntheses occur mainly in liver, adipose, and lactating breast tissues, lipid biosynthesis is also observed in cancerous tissue, which is required for the rapid proliferation of cancer cells. It was previously reported that a shift from lipid uptake to de novo lipogenesis in cancer cells leads to increased membrane lipid saturation, resulting in higher levels of saturated and monounsaturated phospholipids, potentially protecting cancer cells from any oxidative damage by reducing lipid peroxidation.

Saturation degree of phospholipids can determined from the ratio of specific peaks of lipids Raman spectra. In real bio-environment (cells, tissue), this characterization of degree of saturation works only if measured profiles present lipid Raman spectra, which are not significantly distorted by other biomolecular profiles, mostly proteins, as their spectral peaks are overlapped with those of lipids.

This strategy was applied to cellular lipid droplets and extracellular matrix where the lipid component is prevailing. However, the saturation degree of intracellular lipid structures (membranes, envelopes) cannot be estimated directly from the measured Raman spectra of cellular organelles due to the fact that intracellular Raman spectra usually are a mixture of biomolecular components (mostly proteins, lipids and nucleic acids) and characteristic peaks of the lipid component are considerably distorted.

Based on the foregoing, there is an ongoing and unmet need for improved methods of determining the biomolecular components of cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a fuller understanding of the nature and objects of the disclosure, reference should be made to the following detailed description taken in conjunction with the accompanying figures.

DETAILED DESCRIPTION OF THE DISCLOSURE

Figure 1:
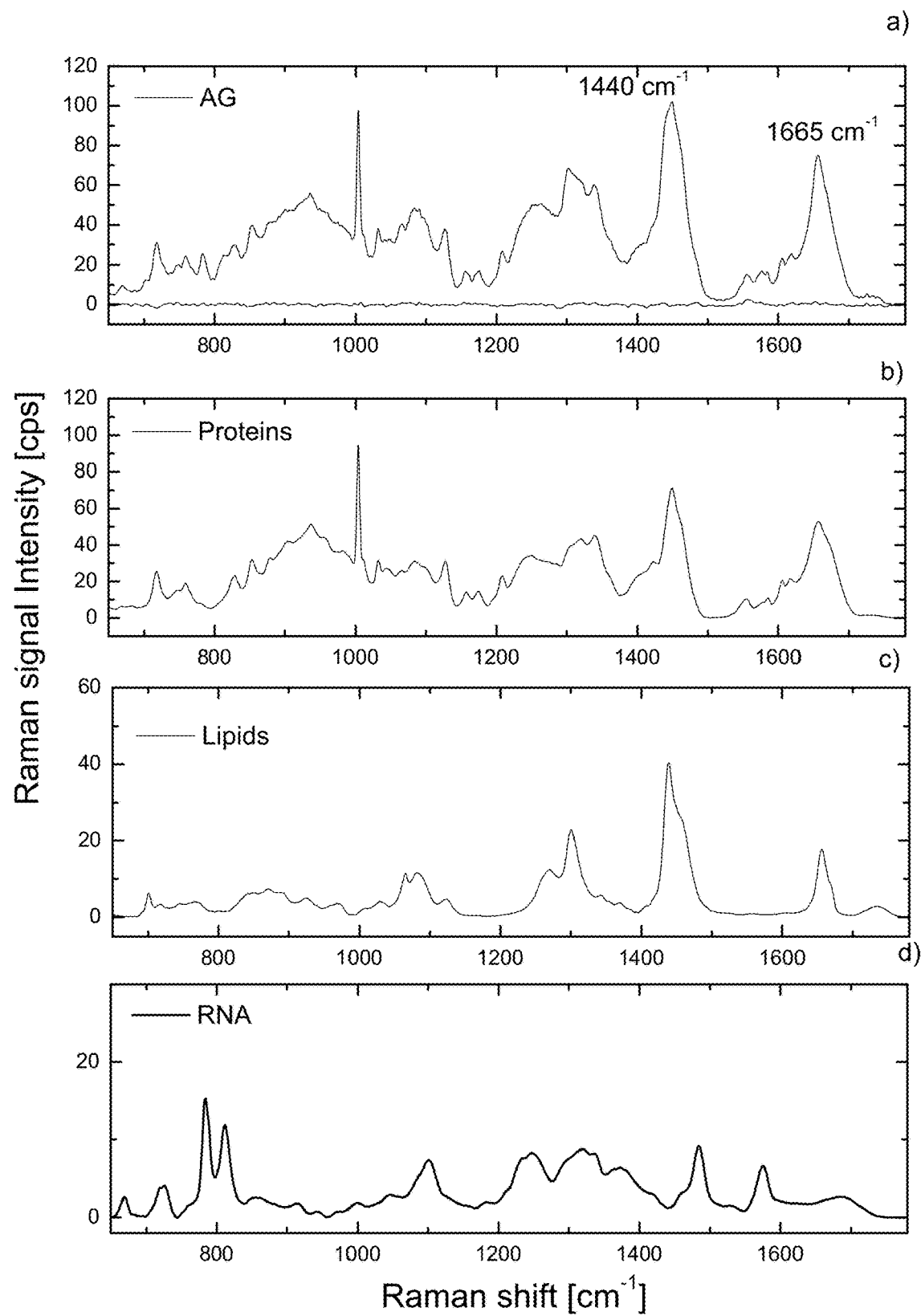
FIG. 1 shows a Raman spectrum of apparatus Golgi measured in live HeLa cell (a) and spectra of biomolecular components in this organelle—proteins (b), lipids (c) and RNA (d). Proteins component have major overlap almost in all range of lipid spectrum.
Figure 2:
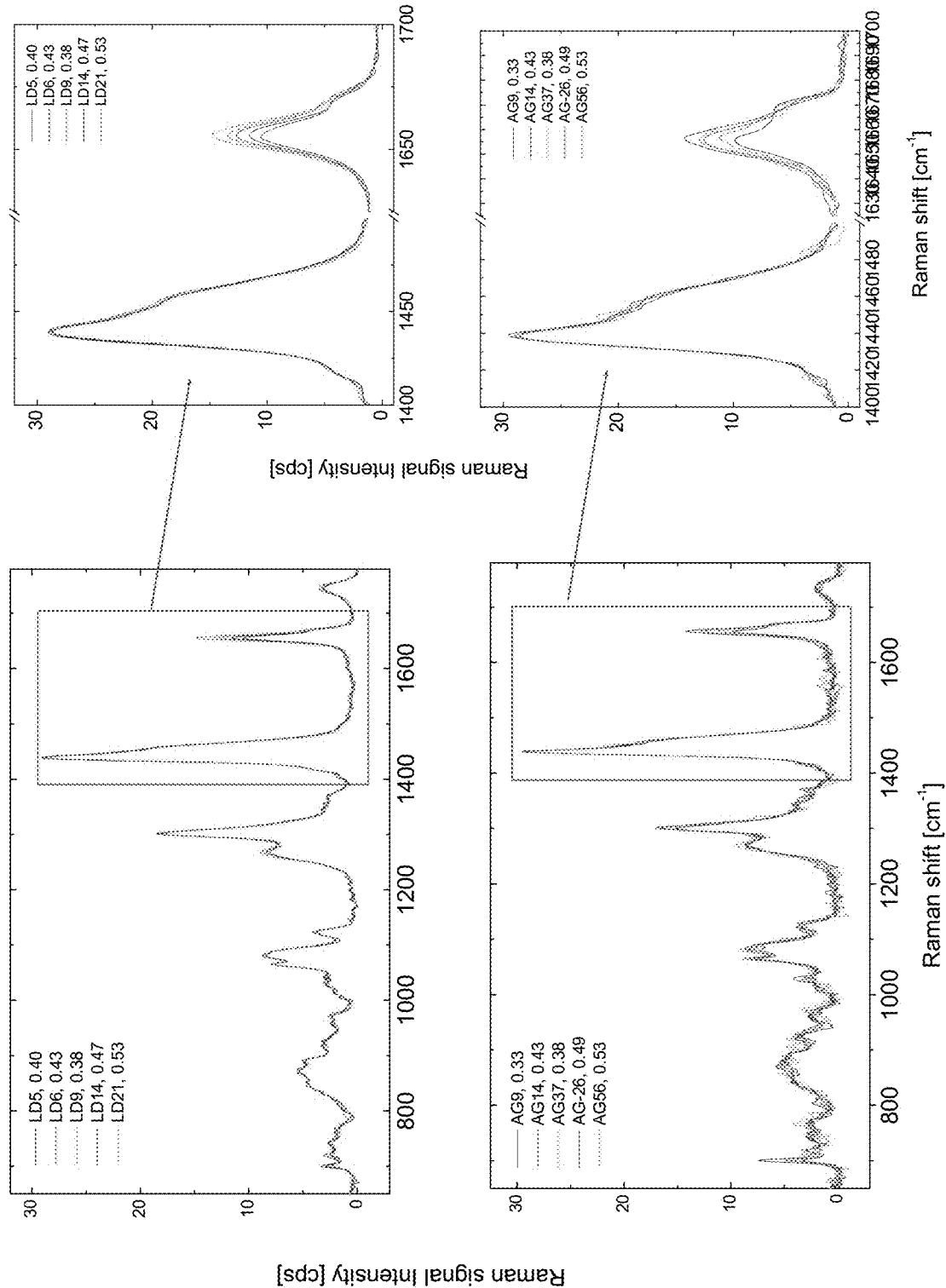
FIG. 2 shows Raman spectra of random chosen lipid droplets (LD, upper panel, spectra preprocessed only) and lipids in apparatus Golgi (AG, lower panel, spectra derived by BCA from preprocessed spectra of organelles) of HeLa cells. Numbers represent number of cell and corresponding parameter of lipids saturation.
Figure 3:
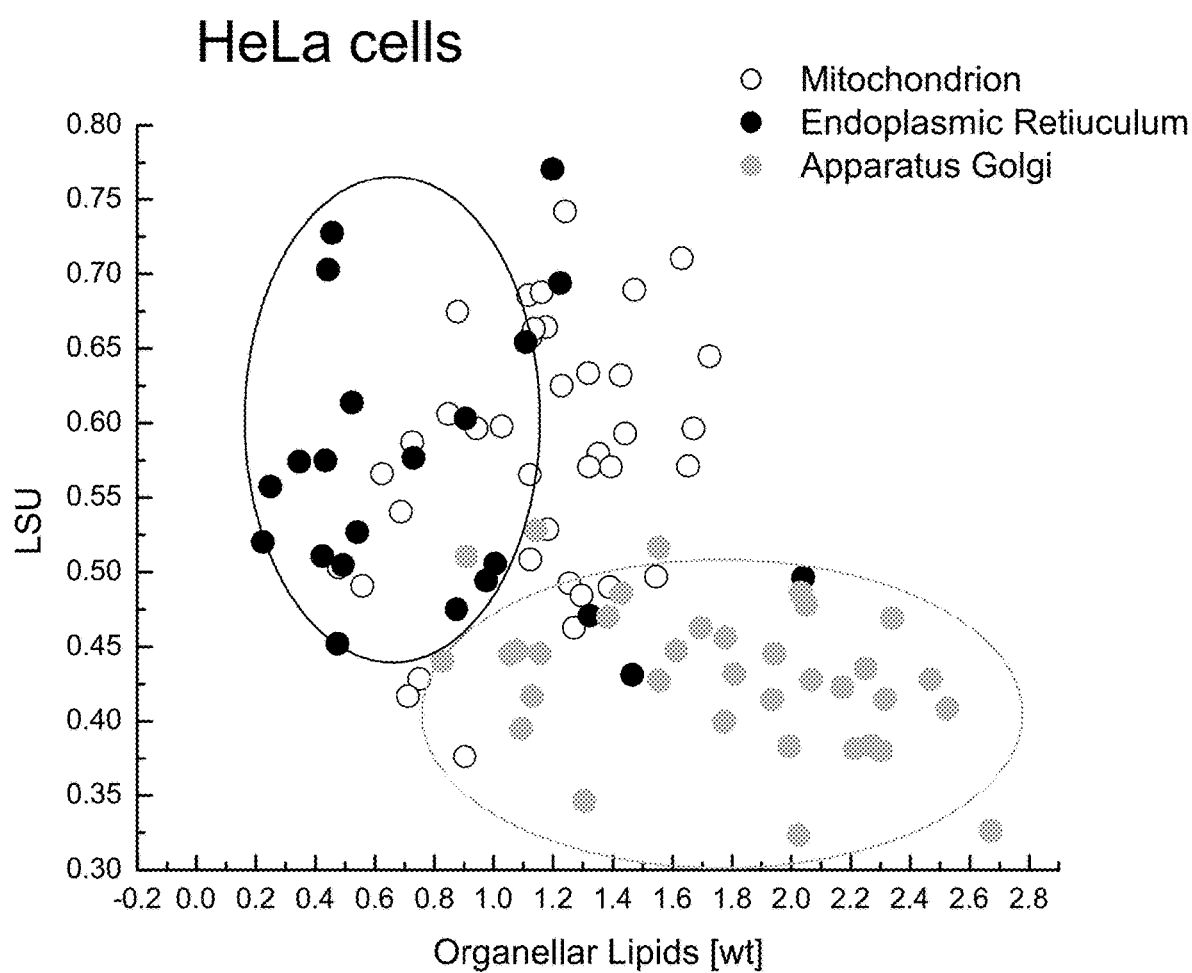
FIG. 3 shows an example of LSU (lipid saturation parameter) versus corresponding organellar lipid concentrations in mitochondria, ER and AG of HeLa cells. AG LSU cluster is not strongly overlapped with these of ER and mitochondrion.
Figure 4:
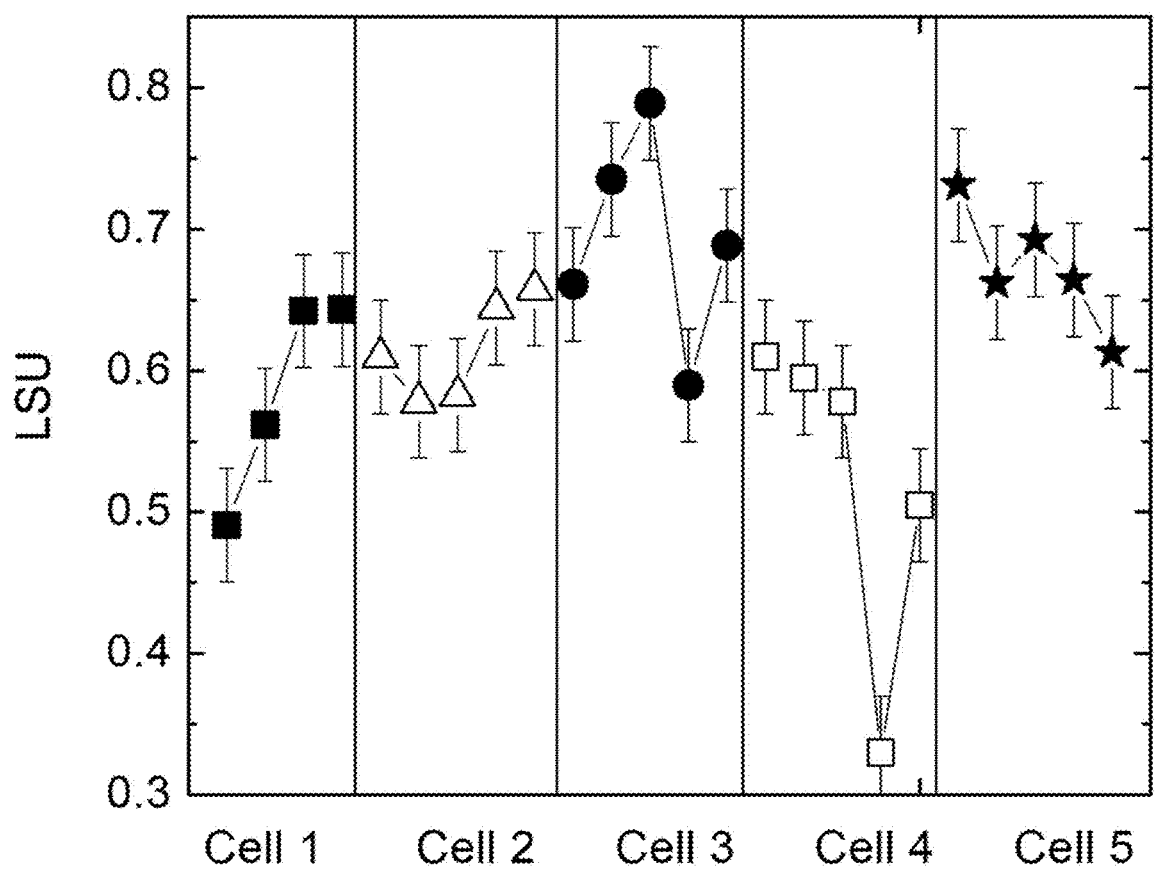
FIG. 4 shows diversity of LSU (ER) in the same single cell.
Figure 5:
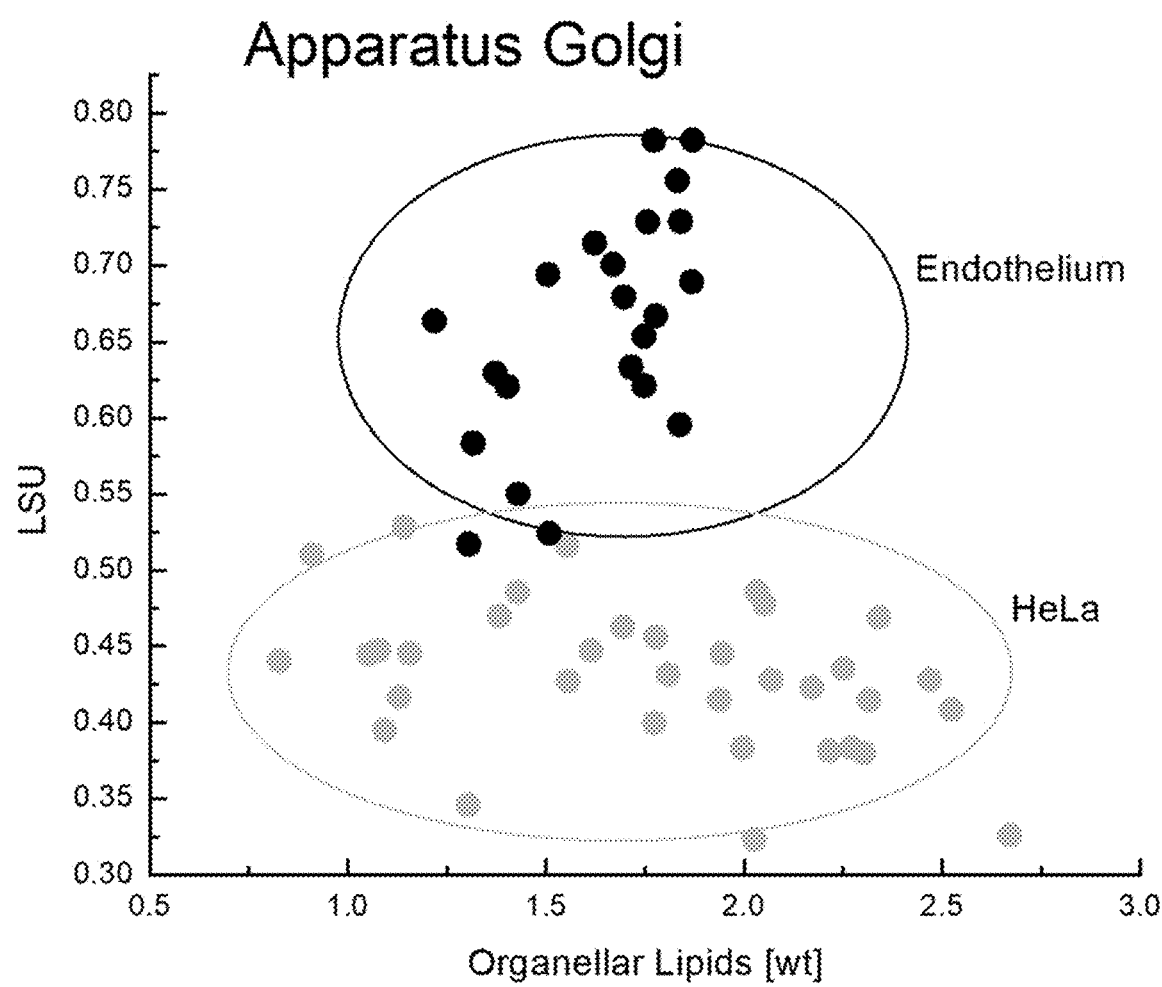
FIG. 5 shows difference of LSU in AG of cancerous (HeLa) and normal (Endothelium) cell lines.

Although claimed subject matter will be described in terms of certain examples, other examples, including examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides methods of lipid measurement in cells. The present disclosure also provides uses of the methods. For example, the methods are used in the diagnosis of cancerous cells.

For example, the present disclosure provides methods to determine the saturation degree of intracellular lipids from the Raman spectrum of an organelle by application of biomolecular component analysis (BCA). BCA is based on an accurate spectral fit of the measured Raman spectrum to a model Raman spectrum, generated by a linear summation of the weighted spectra of the basic molecular components. In mathematical terms, the Raman spectrum of a measured cellular domain $r_{total} = c_1 r_1 + c_2 r_2 + \ldots + c_i r_i$, where $r_i$ is the Raman spectrum and $c_i$ is a weight of the $i_{th}$ component. The weights, or the specific contributions of the each component into model $r_{total}$ relate to the macromolecular concentrations. If all component spectral profiles, $r_i$, are known, the model can then be generated by any mathematical fitting, such as the least-squares algorithm.

In practice, biomolecular modeling of intracellular Raman spectra is based on a set of the major classes of macromolecules—proteins, nucleic acids, lipids and saccharides, which collectively make major contributions to the nonelastic scattering intensities, thereby, the component set may be limited to five spectra of these biomolecules.

Well-established component spectra for nucleic acids, saccharides (mostly presented as glycogen) and proteins in specific organelles allow for the assumption that after subtraction of the contributions of all these weighted components from the measured Raman spectrum, a residual Raman profile can be assigned to the contribution of lipids.

Saturation degree of phospholipids can be estimated (e.g., determined) from ratio of specific peaks of lipids Raman spectra. For example, the characteristic peaks in the Raman scattering spectra at 1,656 cm$^{-1}$ (cis C=C stretching mode) and 1,445 cm$^{-1}$ (CH$_2$ scissoring mode) can be used as markers defining the ratio of unsaturated-to-saturated carbon-carbon bonds of the fatty acids in the lipids.

In an aspect, the present disclosure provides methods of lipid measurement in cells. In various examples, the methods are used to determine the presence and/or absence of lipid(s) in a cell (or a portion thereof), and, if lipid(s) are present in the cell (or portion thereof), optionally, the presence and/or absence of the saturated and/or unsaturated lipid(s) and/or the amount (e.g., relative amount) of saturated and/or unsaturated lipids in the cell (or portion thereof). The term "lipid" as used in this disclosure includes, but is not limited to, phospholipids.

In various examples, a method for determining a lipid composition in a portion of a cell comprises: determining the Raman spectrum of the portion of the cell; optionally, determining a model Raman spectrum (e.g., a reference Raman spectrum) corresponding to the portion of the cell, and comparing the Raman spectrum of the portion of the cell with a model Raman spectrum, which does not include a lipid component (e.g., subtracting a model Raman spectrum from the Raman spectrum of the portion of the cell), where the difference between the Raman spectrum of the portion of the cell and the model Raman spectrum (e.g., a residual Raman spectrum) correlates to the lipid composition in the portion of the cell (e.g., the presence and/or absence of lipid(s)).

Determining the Raman spectrum of the portion of the cell can be carried out in various ways. For example, the determining the Raman spectrum of the portion of the cell comprises: contacting (e.g., irradiating or exposing) the portion of a cell with radiation having a wavelength of 400 nm to 1200 nm (including all integer nm values and ranges therebetween), where at least a portion of the radiation is scattered, and detecting the scattered radiation. Methods of determining (e.g., measuring) Raman spectra are known in the art.

The Raman spectrum of the portion of the cell and various components of the model Raman spectrum can be obtained using various systems/instruments. In various examples, a microRaman system/instrument, such as, for example, a DXR2 Raman microspectrometer (available from ThermoFisher Scientific, USA) is used. Examples of suitable systems/instruments are known in the art.

The Raman spectrum of the portion of the cell and/or the model Raman spectrum and/or the residual Raman spectrum can comprise various wavelengths. For example, the Raman spectrum of the portion of the cell and/or the model Raman spectrum and/or the residual Raman spectrum comprise(s) wavelengths from 200 cm$^{-1}$ to 3200 cm$^{-1}$ (e.g., 200 cm$^{-1}$ to 1800 cm$^{-1}$), including all cm$^{-1}$ values and ranges therebetween.

The model Raman spectrum of the portion of the cell can be determined in various ways. For example, the model Raman spectrum is a combination (e.g., a linear combination) of two or more Raman spectra of cellular components other than lipid(s) and each Raman spectrum is a Raman spectrum of a different cellular component.

The model Raman spectrum is a Raman spectrum of one or more cellular components. The model Raman spectrum may be referred to as a reference Raman spectrum. In various examples, the model Raman spectrum does not include a lipid component. The non-lipid cellular components used to determine the model Raman spectrum are chosen from proteins, RNA, DNA, polysaccharides, saccharides, and combinations thereof.

In various examples, the model Raman spectrum is a combination of Raman spectra of cellular components (e.g., a model Raman spectrum comprises one, two, three, four, or five cellular components Raman spectra). In the case where the model Raman spectrum is a combination of two or more cellular component Raman spectra, the individual spectra in the combination may be weighted to minimize the residual spectrum.

The model Raman spectrum may be determined using Raman spectra of cellular component(s) obtained from a previously developed database/library of Raman spectra of cellular components. In various examples, the two or more Raman spectra of cellular components other than lipid(s) are obtained from a database of Raman spectra of cellular components.

The presence and/or absence of lipids in the portion of the cell is determined by comparing the Raman spectrum of the portion of the cell with a model Raman spectrum (e.g., subtracting a model Raman spectrum from the Raman spectrum of the portion of the cell), where the difference between the Raman spectrum of the portion of the cell and a model Raman (e.g., the residual Raman spectrum) correlates to the lipid composition in the portion of the cell (e.g., the presence and/or absence of lipid(s) in the portion of the cell).

A residual Raman spectrum may be determined by subtraction of a model Raman spectrum from a Raman spectrum of the portion of the cell. In various examples, a method comprises minimization of the residual Raman spectrum. In the case where the model Raman spectrum comprises a lipid component Raman spectrum, the residual Raman spectrum may be zero. In the case where the model Raman spectrum does not comprise a lipid component Raman spectrum, the residual Raman spectrum correlates (e.g., is equal to) the lipid Raman spectrum.

Using appropriate calibration (e.g., calibration curves), the total amount of lipid in a portion of a cell can be determined. In various examples, lipid amounts of 0.2 mg/ml to 100% lipid are determined.

The comparison may comprise minimizing the residual Raman spectrum resulting from comparison of the model Raman spectrum and Raman spectrum of the portion of the cell. For example, the comparison comprises adjusting the weighting of the two or more Raman spectra to minimize the residual Raman spectrum. The weighting may be determined by mathematical fitting (e.g., least squares fitting) of the model Raman spectrum to the Raman spectrum of the portion of the cell.

The methods can be used to determine the presence and/or absence of lipids in a cell. By repeating the method on different portions of a cell and/or different cells, the presence and/or absence of lipids in a cell and/or a plurality of cells can be determined.

In the case where lipids are present, the methods can also be used to determine the relative amounts of saturated lipids to unsaturated lipids. In an example, in the case where lipids are present, the methods are used to determine the ratio of saturated lipids to unsaturated lipids. In the case where unsaturated lipids are present, the degree of saturation of the unsaturated lipids and/or the stereochemistry (e.g., presence and/or absence of lipid(s) with cis and/or trans carbon-carbon double bonds) of the unsaturated lipids may also be determined.

The portion a cell can comprise various parts of a cell. In various examples, the portion of a cell comprises one or more a cellular component. Non-limiting examples of cellular components include a cell membranes, mitochondria, Golgi apparatus, lipid droplets, lysosomes, endoplasmic reticulum, endosomes, nuclei, nucleoli, vacuoles and the like.

The portion of a cell can be from various cells. In various examples, the portion of a cell is from an isolated cell (e.g., a cell isolated from, for example, organ, tissue, bodily fluids, and the like from an individual). The portion of a cell may be from a live or fixed cell.

The portion of a cell may be from a selected portion of the cell. Accordingly, in an example, a method further comprises staining a cell to select the portion of the cell (e.g., a selected cellular component, such as, for example, a cellular structure). Examples of staining to identify particular portions of a cell (e.g., a particular cellular component, such as, for example, a particular cellular structure) are known in the art.

The portion of a cell can be of various sizes (e.g., volumes). In various example, the portion of the cell has a volume of 1 cubic micron to 10 cubic microns, including all 0.1 cubic micron values and ranges therebetween. A plurality of portions of a cell may be combined such that Raman spectra for the multiple portions of the cell are obtained.

The Raman spectrum of the portion(s) of a cell and/or cellular component(s) can be obtained using various excitation radiation (e.g., sources and wavelengths). In various examples, the excitation radiation is laser radiation (e.g., infrared laser radiation). Non-limiting examples of suitable laser radiation include those comprising one or more wavelengths of 450-1100 nm (e.g., 488 nm, 532 nm, 632 nm, 785 nm, 1064 nm, and the like), including all nm values and ranges therebetween. In an example, the excitation radiation is laser radiation (e.g., laser diode radiation) having a one or more wavelengths of 630-680 nm, including all nm values and ranges therebetween.

The portion of a cell may be present on a substrate. For example, the portion of the cell is from a cell disposed on a glass substrate. A low Raman background substrate can be used Examples of low Raman background substrates are known in the art. Non-limiting examples of suitable substrates include $CaF_2$, $BaF_2$, silicon, and the like. In an example, the substrate is luminescence free grade glass (e.g., having a thickness 150-170 microns, including every 0.1 micron value and range therebetween). It may be desirable to use such substrates if, for example, an oil immersion 100× objective lens is used.

The following describes various facets of methods of the present disclosure:

1) In various examples, the methods are carried out using a Raman microspectrometer. Any microspectrometer, which provides spatial resolution sufficient for measurement of Raman spectrum of single organelle, and quality of spectrum (noise-to-signal ratio, NSR) sufficient for biomolecular component analysis resulting in residual spectrum with intensities close to standard measurement error, can be used. It is desirable that a Raman microspectrometer with lateral spatial resolution of at least about ~1 um (e.g., using a 100× oil immersion objective lens), spectral resolution less than 2 $cm^{-1}$, and NSR of less than 5% is used. The Raman microspectrometer can have a laser excitation source. Wavelength(s) of laser excitation source for Raman microspectrometer may be any wavelength(s) that produce moderate background signal to avoid strong distortion of cellular Raman spectrum. For example, it is desirable to use an excitation wavelength in the visible red region (e.g., 632 nm), which produces less unwanted background comparing to NIR sources and less destructive for live cells as sources in blue and green visible region.

2) Cell/tissue sample environment. Cells can be grown (tissue slices can be placed) on the substrate, which produces low spectral background, such as, for example, free luminescence glass substrate. If cells/tissue stained by specific dye for organelle visualization, it is desirable that the excitation spectrum of the dye should not be overlapped with the Raman excitation source to avoid unwanted luminescence background.

3) Spectrum measurement. a) For example, after the placing of the substrate with cells at the microscope stage, at least ~5 minutes before first measurement substrate should be kept untouched. This time is necessary for temperature and mechanical stabilization to avoid mechanical movement of bottom glass during measurements. b) Cell site/organelle chosen for measurements should be carefully focused (z-stage) and targeted for beam waist position overlapping (x-y stage). c) For 632 nm laser source, an desirable laser excitation power on the sample with CCD accumulation time were found to be ~30 mW @60 s. d) It may be desirable to recheck that targeted site of the sample before the measurement is started.

4) Preprocessing of measured spectrum. Subtraction of background and correction of baseline is applied to measured spectrum, for example using specific software. For example, this subtraction/correction procedure was incorporated to the software tool-box of Biomolecular Component Analysis software.

5) Biomolecular Component Analysis. For example, a preprocessed spectrum is analyzed by specific software toolbox: Biomolecular Component Analysis (BCA). BCA is based on an accurate spectral fit of the measured Raman spectrum to a model Raman spectrum, generated by a linear summation of the weighted spectra of the basic molecular components. In mathematical terms, the Raman spectrum of a measured cellular domain $r_{total}=c_1 r_1 + c_2 r_2 + \ldots c_i r_i$, where $r_i$ is the Raman spectrum and $c_i$ is a weight of the $i_{th}$ component. The weights, or the specific contributions of the each component into the model, relate to the macromolecular concentrations. If all component spectral profiles, $r_i$, are known, the model can then be generated by any mathematical fitting, such as the least-squares algorithm.

6) Obtaining of Lipids spectrum from measured spectrum. Spectrum of organellar lipids is obtained by subtraction of all weighted biomolecular components (except lipids) from preprocessed organellar measured spectrum.

7) Assessment of organellar lipids unsaturation degree. Ratio of the characteristic peaks at 1,656 cm$^{-1}$ (cis C=C stretching mode) and 1,445 cm$^{-1}$ (CH$_2$ scissoring mode) in the lipid Raman spectrum are used as markers defining the ratio of unsaturated-to-saturated carbon-carbon bonds of the fatty acids in the lipids.

In various examples, a method of the present disclosure comprises one or more of these facets. FIGS. 1-5 describe data obtained using methods of the present disclosure (e.g., methods comprising one or more of these facets).

In an aspect, the methods of the present disclosure and/or data obtained using the methods can be used in methods of diagnosing a disease state in an individual. Various disease states can be diagnosed. Non-limiting examples of disease states include cancers, certain neurodegeneration diseases, radiation sickness, and the like. Without intending to be bound by any particular theory, it is considered that the presence of increased levels of saturated and monounsaturated phospholipids is indicative that a cell is abnormal or damaged.

In an example, a method of determining the presence and/or absence of abnormal or damaged cells in an individual comprises subjecting a cell or cells to a method of the present disclosure. The levels of saturated and monounsaturated phospholipids is a quantitative marker of pathological lipid metabolism associated with various diseases such as, for example, cancers. For example, the ratio of certain types of lipids is indicative of cancers such as, for example, breast cancers, prostate cancers, and the like.

An individual can be a human or non-human mammal. Non-limiting examples of non-human mammals include cows, pigs, mice, rats, rabbits, cats, dogs, or other agricultural, pet, or service animals, and the like.

The steps of the method described in the various examples disclosed herein are sufficient to carry out the methods of the present disclosure. Thus, in an example, the method consists essentially of a combination of the steps of the methods disclosed herein. In another example, the method consists of such steps.

The following Statements describe various non-limiting examples of methods of the present disclosure:

Statement 1. A method for determining a lipid composition in a portion of a cell comprising:

determining the Raman spectrum of the portion of the cell;

optionally, determining a model Raman spectrum corresponding to the portion of the cell; and comparing the Raman spectrum of the portion of the cell with a model Raman spectrum, which does not include the lipid component (e.g., subtracting a model Raman spectrum from the Raman spectrum of the portion of the cell to provide a residual Raman spectrum), where the difference between the Raman spectrum of the portion of the cell and the model Raman spectrum (e.g., in the case where the model Raman spectrum does not include lipid component(s)), the residual Raman spectrum) correlates to the lipid (e.g., phospholipid) composition in the portion of the cell (e.g., the presence and/or absence of lipid(s) (e.g., phospholipid(s)) in the portion of the cell)).

Statement 2. A method according to Statement 1, where the determining the Raman spectrum of the portion of the cell comprises:

contacting the portion of the cell with radiation having a wavelength of 400 nm to 1200 nm, where at least a portion of the radiation is scattered; and detecting the scattered radiation.

Statement 3. A method according to Statement 1 or 2, where the Raman spectrum of the portion of the cell and the model Raman spectrum, or the residual Raman spectrum, comprise(s) wavelengths from 200 cm$^{-1}$ to 3200 cm$^{-1}$ (e.g., 200 cm$^{-1}$ to 1800 cm$^{-1}$).

Statement 4. A method according to any one of the preceding Statements, where the model Raman spectrum is a combination (e.g., a linear combination) of two or more Raman spectra of cellular components other than lipid(s) and each Raman spectra is a Raman spectrum of a different cellular component.

Statement 5. A method according to Statement 4, where the two or more Raman spectra of cellular components other than lipid(s) are obtained from a database of Raman spectra of cellular components.

Statement 6. A method according to Statement 4 or 5, where the cellular components are chosen from proteins, RNA, DNA, polysaccharides, saccharides, and combinations thereof.

Statement 7. A method according to any one of the preceding Statements, where in the comparison comprises minimizing the residual Raman spectrum resulting from comparison of the model Raman spectrum and Raman spectrum of the portion of the cell.

Statement 8. A method according to Statement 7, where the comparison comprises adjusting the weighting of the two or more Raman spectra to minimize the residual Raman spectrum.

Statement 9. A method according to Statement 8, where the weighting is determined by mathematical fitting (e.g., least squares fitting) of the model Raman spectrum to the Raman spectrum of the portion of the cell.

Statement 10. A method according to any one of the preceding Statements, where the relative amounts (e.g., ratio) of saturated lipids to unsaturated lipids is determined.

Statement 11. A method according to any one of the preceding Statements, where, in the case where unsaturated lipids are present in the portion of the cellular structure, the degree of saturation of the unsaturated lipids is determined.

Statement 12. A method according to any one of the preceding Statements, where, in the case where unsaturated lipids are present in the portion of the cellular structure, the stereochemistry (e.g., presence and/or absence of lipid(s) with cis and/or trans carbon-carbon double bonds) of the unsaturated lipids is determined.

Statement 13. A method according to any one of the preceding Statements, where the portion of a cell is from a cellular component (e.g., a cellular component such as, for example, a cell membranes, mitochondria, Golgi apparatus, lipid droplets, lysosomes, endoplasmic reticulum, endosomes, nuclei, nucleoli, vacuoles, and the like).

Statement 14. A method according to any one of the preceding Statements, where the portion of a cell is from an isolated cell (e.g., a cell isolated from, for example, an organ, tissue, bodily fluids, and the like from an individual).

Statement 15. A method according to any one of the preceding Statements, where the portion of a cell is from a live or fixed cell.

Statement 16. A method according to any one of the preceding Statements, further comprising staining a cell to identify and/or select the portion of the cell.

Statement 17. A method according to any one of the preceding Statements, where the portion of the cell has a volume of 1 cubic micron to 10 cubic microns.

Statement 18. A method according to any one of the preceding Statements, where the radiation is laser radiation (e.g., infrared laser radiation).

Statement 19. A method according to Statement 18, where the laser radiation has (e.g., comprises) a wavelength of 488 nm, 532 nm, 632 nm, 785 nm, or 1064 nm.

Statement 20. A method according to any one of the preceding Statements, where the portion of the cell is from a cell disposed on a substrate (e.g., a substrate disclosed herein such as, for example, a glass substrate).

Statement 21. A method according to any one of the preceding Statements, further comprising diagnosing a disease (e.g., cancer, such as, for example, breast cancer, prostate cancer, and the like) in an individual (e.g., via the presence and/or absence of abnormal or damaged cells in an individual).

The following examples are presented to illustrate the present disclosure. They are not intended to be limiting in any matter.

Example 1

This example provides examples of methods of the present disclosure and data obtained using methods of the present disclosure.

The following methods were used to generate the data shown in FIGS. 1-5.

MicroRaman spectrometer equipment. Standard DXR2 model was equipped by special 633 nm @70 mW Laser Diode module (ROUSB-633-PLR-70-1, Ondax) to obtain ~33 mW of excitation power on the sample. Fluorescence Illuminator with green fluorescence Cube (510-550 nm) and X-Cyte™ 120-PC (Photonic Solutions Inc.) mercury lamp were installed for visualization of labelled cellular organelles. Options of high resolution grating at 633 nm and Olympus Plan N 100× (NA=1.25) oil immersion objective lens were chosen for Raman spectra acquisition to be compatible with BCA toolbox.

Measurement reproducibility. To determined standard deviations of DXR2, Raman spectra of freshly extracted white egg were measured at the accumulation times used in experiments with the cell culture. Protein concentration in white egg is close to that of intracellular proteins to mimic a homogeneous biomolecular medium. The standard deviations were found to be below 5%, which warrants reproducible BCA measurements.

Subtraction of Raman background. An internal algorithm in BCA toolbox for automatic subtraction of background from the acquired spectra of the cells on glass bottom was developed. To ensure the accuracy of this procedure, all background components for glass-bottom Petri dishes were measured, smoothed and normalized to be used by software procedure for background subtraction.

Device Calibration. The Raman micro-spectrometer system was calibrated for measurements of absolute concentrations of proteins, DNA, RNA, lipids and saccharides using solutions of bovine serum albumin (Sigma A3912), calf thymus DNA (Sigma D1501), *S. cerevisiae* RNA (Sigma 83853), bovine brain lipids (Avanti lipids 131101P) and Type IX glycogen from bovine liver (Sigma G0885). To avoid fast evaporation, measurements of lipid solution in chloroform were done in a sealed capillary. Raman profiles of the BCA components for initial modelling were measured using HeLa DNA extract for DNA component and HeLa RNA extract for RNA component. Lipid component was measured in lipid droplets of HeLa live cells. Initial organellar protein profiles were obtained by subtraction of the other weighted BCA components. Then, as measured data were accumulated, profiles of RNA, DNA and proteins were specified more accurately, using BCA feedback procedures. Biomolecular components were calibrated to 100 mg/ml for proteins and 20 mg/ml for RNA, DNA, lipids and glycogen.

BCA toolbox description. BCA toolbox is a stand-alone software package, which works with single raw Raman spectrum measured in the cell on the glass-bottom dish. The program consists of three main blocks: the background processing and subtraction block, the nonlinear least squares routine block, and the graphic user interface. As input data were included: (i) measured cellular spectrum; (ii) choice of cellular organelle where this spectrum was measured (nucleus, nucleolus, mitochondrion, endoplasmic reticulum, apparatus Golgi for growing cell; chromosome or cytoplasmic areas for mitotic cell); (iii) choice of live or fixed (formaldehyde, ethanol) cell. Toolbox delivers the following outputs: (i) background free Raman spectrum, (ii) residual spectrum for estimation of modelling quality, (iii) weight coefficients for five biomolecular components (proteins, DNA, RNA, lipids, glycogen), (iv) ratio of 1665 $cm^{-1}$ to 1440 $cm^{-1}$ lipid peaks as a parameter of saturation degree of phospholipids. As additional output data software generates a file with a spectrum of organellar phospholipids (result of subtraction of weighted profiles of proteins, DNA, RNA and glycogen from background free organellar spectrum).

Cell culture. The measurements were performed on the HeLa cells grown in conventional glass bottom dishes (Mattek Co, Ashland, Mass.), and cultured in Advanced DMEM (ThermoFisher Scientific, Grand Island, N.Y., USA), supplemented with 3% fetal calf serum (ThermoFisher Scientific, Grand Island, N.Y., USA), GlutaMAX (ThermoFisher Scientific, Grand Island, N.Y., USA), antibiotic-antimycotic solution (ThermoFisher Scientific, Grand Island, N.Y., USA) at 37° C. in a humidified atmosphere containing 5% $CO_2$. Before Raman spectroscopy measurements the cells were transferred into the optically transparent DMEM (ThermoFisher, Grand Island, N.Y.) supplemented with 25 mM of HEPES.

Mitochondria, Endoplasmic Reticulum and Golgi Apparatus labelling. Cytoplasmic organelles were labeled by commercial fluorescent reporters to enable targeted acquisition of Raman spectra in these cellular organelles. The mitochondria were labeled with MitoTrecker Green FM (ThermoFisher Scientific, Grand Island, N.Y.); ER with ER-Tracker Green (ThermoFisher Scientific, Grand Island, N.Y.); and Apparatus Golgi at with NBD C6 ceramide-BSA (ThermoFisher Scientific, Grand Island, N.Y.), in accordance with the manufacturer's instructions. The organelle stains generated weak additional Raman signal in cells, which was then taken into account by software procedure for background subtraction.

Measurement parameters and BCA accuracy. Accumulation parameter was 6×20 seconds for each spectrum acquisition was found to meet signal/noise ratio requirement to satisfy the good quality of BCA from one side, and to avoid unwanted phototoxicity from the other side. Before the first measurement, dish was kept untouched at least ~5 minutes. This time was necessary for temperature and mechanical stabilization to avoid mechanical movement of bottom glass during measurements. The quality of model fit for organellar BCA was estimated by comparing the residual intensities over the significant wavelength range with standard error produced by DXR2 during measurement of white egg protein mixture (+2-3 counts per second). If residual intensities were larger than this value, the result of measurement was rejected.

Example 2

This example provides examples of methods of the present disclosure and data obtained using methods of the present disclosure.

The methods described in Example 1 were used to generate the data shown in FIGS. 6-11.

Figure 6:
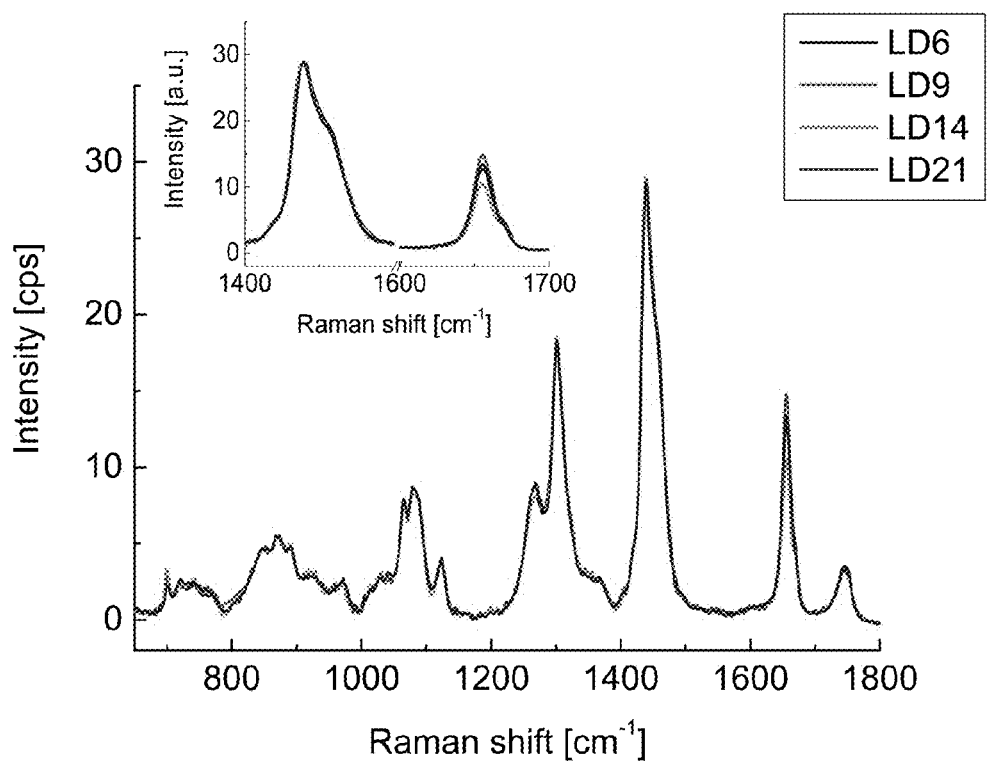
FIG. 6 shows Raman spectra of random chosen lipid droplets (LD, left panel,) and lipids in other organelles (mito—mitochondria, ER—endoplasmic reticulum, AG—apparatus Golgi; right panel). Numbers represent number of cell.
Figure 6:
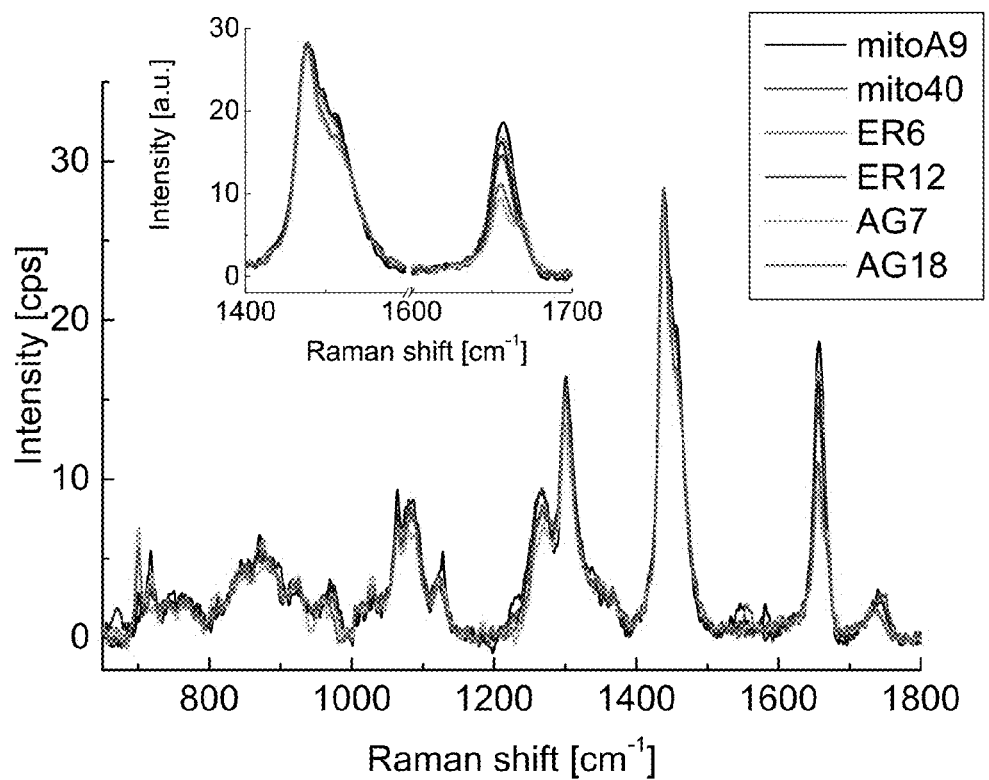

FIG. 6 shows the results of measurements of preprocessed Raman spectra (background subtraction and baseline correction) in large lipid droplets of HeLa cells and lipid Raman spectra in major organelles of HeLa cells, derived by BCA from the preprocessed spectra of corresponding organelles by subtraction of weighted spectra of proteins, RNA and glycogen profiles. For all these samples, BCAbox software was used, (developed by ACIS, LLC).

As is shown, in both cases, profiles of lipids are similar and have different ratios of integrated intensities for characteristic peaks at 1,656 $cm^{-1}$ and 1,445 $cm^{-1}$. Integrated intensities for these peaks were used to estimate the parameter of unsaturation of cellular lipids.

Figure 7:
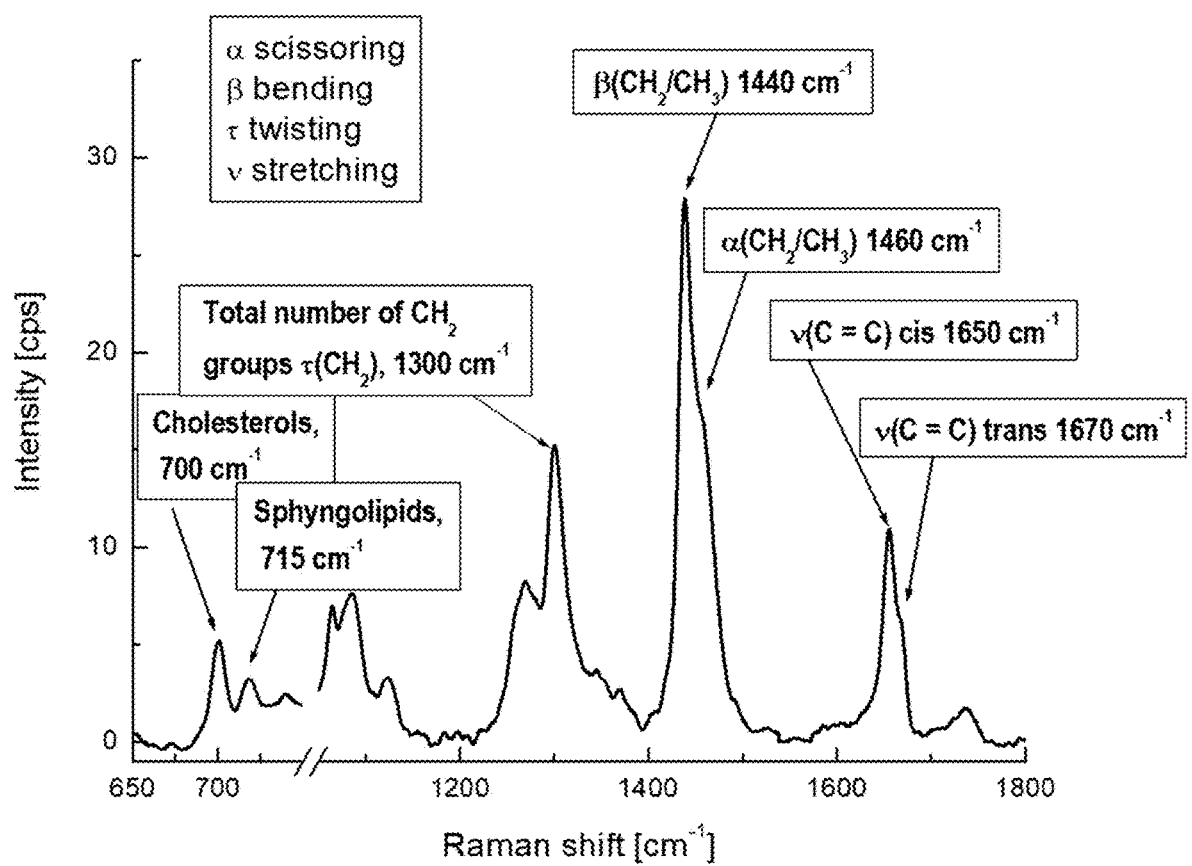
FIG. 7 shows a Raman spectrum of HeLa organellar lipids. Arrows show assigned vibration modes and molecular groups.
Figure 8:
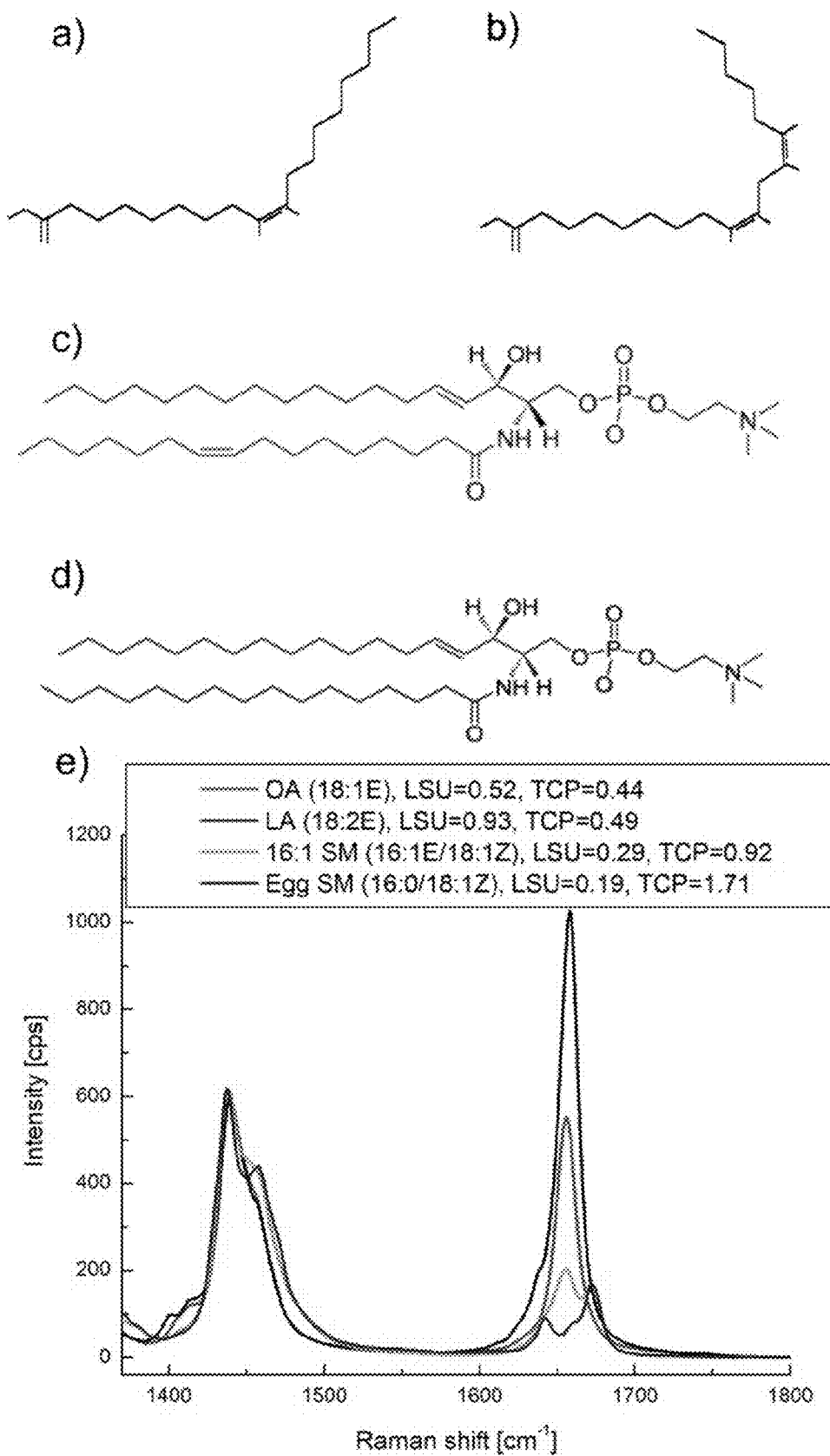
FIG. 8 shows structures of (a) monounsaturated oleic (18:1E), (b) polyunsaturated linoleic (18:2E) acids with the same number of carbon atoms, (c) N-palmitoleoyl-D-erythro-sphingosylphosphorylcholine (16:1E/18:1Z) with one cis and one trans C=C bonds, and (d) chicken egg sphingomyelin (16:0/18:1Z) with one trans C=C bond. Corresponding Raman spectra in the range between 1370 and 1800 $cm^{-1}$ are shown in (c) panel. Abbreviations: OA—oleic acid, LA—linoleic acid, Egg SM—chicken egg sphingomyelin, 16:1 SM—N-palmitoleoyl-D-erythro-sphingosylphosphorylcholine, LSU—lipids unsaturation parameter, TCP—lipids trans/cis parameter. The numbers in parenthesis show a number of carbon bonds (first) and a number of double bonds (second); letter after the second number denotes cis-(E) or trans-(Z) isomer of double bond. Materials: oleic and linoleic acids from Sigma (St. Louis, Mo.); N-palmitoleoyl-D-erythro-sphingosylphosphorylcholine and chicken egg sphingomyelin from Avanti Polar Lipids (Alabaster, Ala.).
Figure 9:
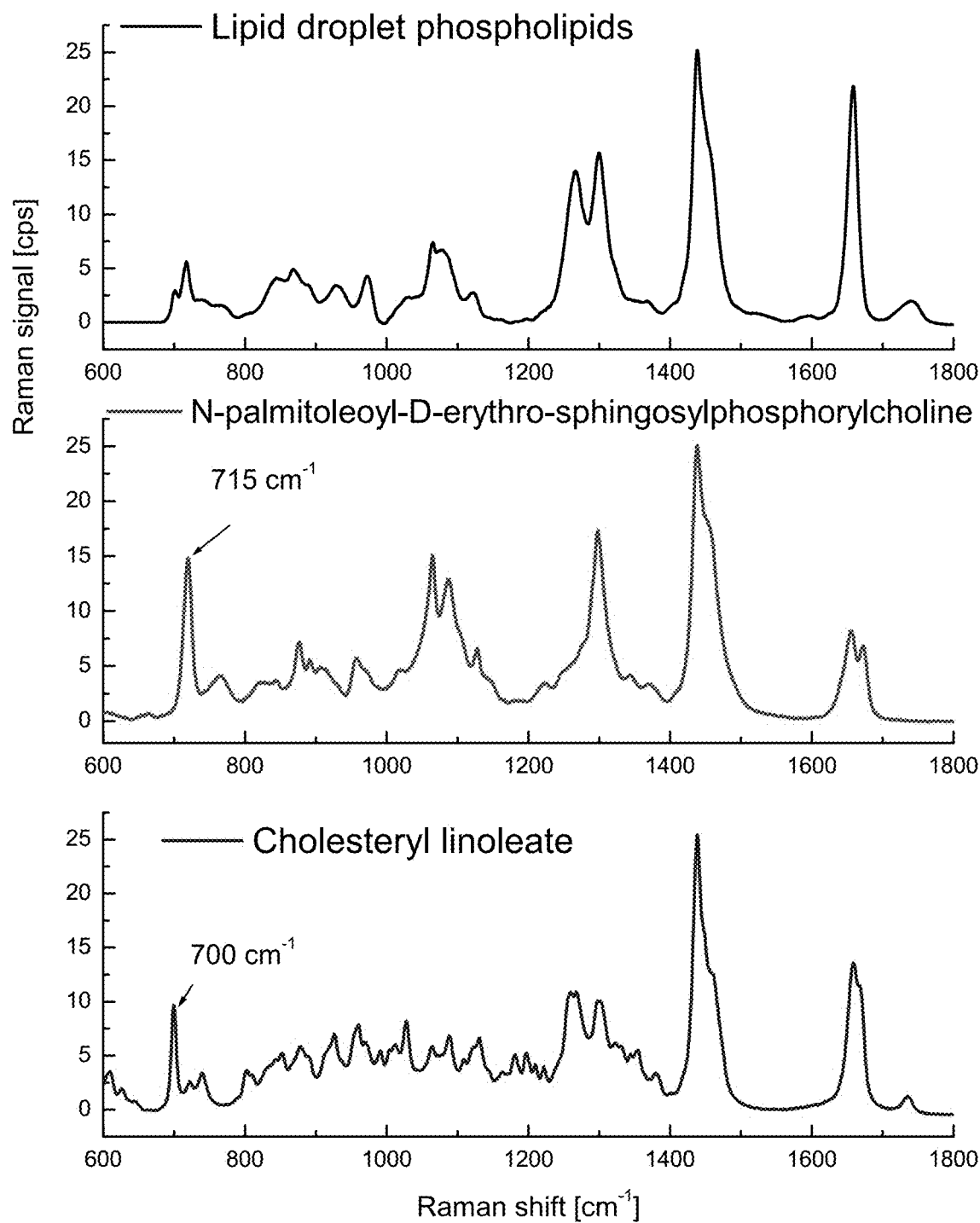
FIG. 9 shows Raman spectra of typical lipid droplet in HeLa cell (upper panel), N-palmitoleoyl-D-erythro-sphingosylphosphorylcholine (middle panel) and Cholesteryl linoleate (lower panel). Characteristic peaks used for identification of sphingolipids and cholesterols are shown by arrows.
Figure 10:
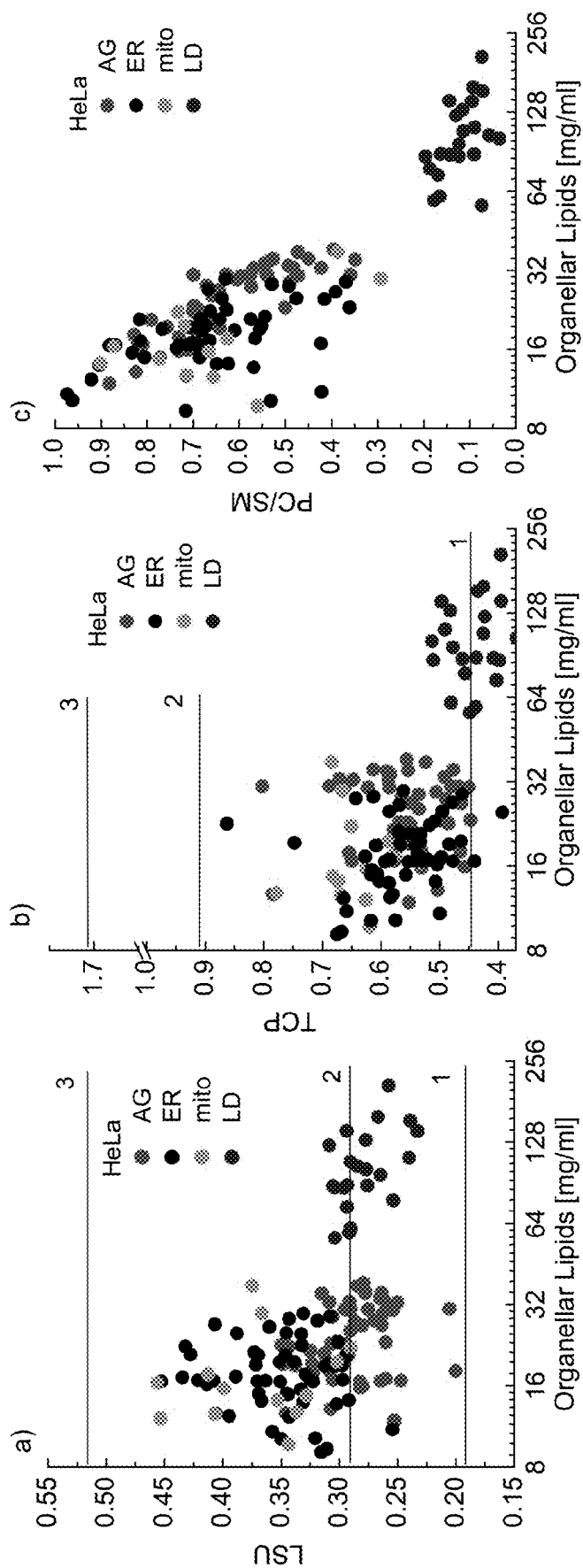
FIG. 10 shows organellar lipidome parameters (LSU, TCP, PC/SM) and lipid concentration in the organelles of HeLa cells. Concentration of lipids vs corresponding LSU as a merit of unsaturation of lipids. (a) TCP as a merit of trans-to cis-ratio of carbon-carbon bonds of cellular lipids (b), and the sphingolipids content PC/SM (c) probed in different organelles of HeLa cells in the same dish. The standard error is comparable to the size of symbols. Abbreviations: AG—apparatus Golgi, ER—endoplasmic reticulum, mito—mitochondrion, LD—lipid droplets. The levels of LSU shown by numbered horizontal lines in graph (a) correspond to: (1) Egg SM (16:0/18:1), LSU=0.19; (2) 16:1 SM (16:1/18:1), LSU=0.29; (3) OA (18:1), LSU=0.52. Levels of TCP shown by numbered horizontal lines in graph (b) correspond to: (1): OA (18:1E), LA (18:2E), TCP-0.45; (2) 16:1 SM (16:1E/18:1Z), TCP=0.92 (3) Egg SM (16:0/18:1Z), TCP=1.71. OA is oleic acid, LA is linoleic acid, Egg SM is chicken egg sphingomyelin and 16:1 SM is N-palmitoleoyl-D-erythro-sphingosylphosphorylcholine. The numbers in parenthesis show the number of carbon bonds (first) and the number of double bonds (second); the letter after the second number denotes cis-(E) or trans-(Z) isomer of the double bond.

FIG. 7 shows details of lipids Raman spectrum and assignments for different vibrational and molecular groups. This information can be used for quantitative estimation of:

a) Phospholipid concentration. The intensity of the peak at 1443 $cm^{-1}$ in lipid spectrum, which is assigned to bending of all $CH_2$ and $CH_3$ molecular bonds, can be used for phospholipid concentration measurement.

b) Unsaturation level of lipids. Areas of two specific spectral bands at 1655 $cm^{-1}$, assigned to the C=C stretching mode, proportional to the amount of unsaturated C=C bonds, and at 1443 $cm^{-1}$, assigned to $CH_2$ scissoring/bending modes, which is proportional to the amount of saturated C—C bonds, can be used for estimation of the unsaturation level of lipids (parameter LSU as a ratio of the corresponding areas). LSU is close to zero for saturated palmitic acid, 0.52 for the monounsaturated oleic acid and 0.93 for the polyunsaturated linoleic acid (FIG. 8)

c) Trans-/Cis-isomers ratio. The ratio of the intensities at 1666 $cm^{-1}$ and 1655 $cm^{-1}$ represents the ratio of trans- to cis-carbon-carbon bond amount in lipid species, and can be used as a quantitative parameter (TCP) for isomers ratio of lipid molecules. For oleic and linoleic acids with only cis-conformation of unsaturated C=C bonds, TCP is equal to 0.45 (FIG. 8), while for phospholipids with one and two trans-C=C bonds, the corresponding parameters are 0.92 and 1.71 respectively.

d) Sphingolipids and Cholesterol content. The presence of cholesterol and sphingolipids in probed organelle can be estimated by the intensity of their corresponding characteristic peaks at ~700 $cm^{-1}$ and 717 $cm^{-1}$, respectively. For pure egg sphingomyelin and N-palmitoleoyl-D-erythro-sphingosylphosphorylcholine (both from Avanti lipids), the PC/SM parameter (sphingolipids content, 717 $cm^{-1}$) is equal to ~1.00. The same value of the cholesterol content (CLA parameter), estimated by 700 $cm^{-1}$ peak intensity, i.e., CLA=1 is resulted from the measured spectra of pure cholesteryl linoleate (FIG. 9).

Figure 11:
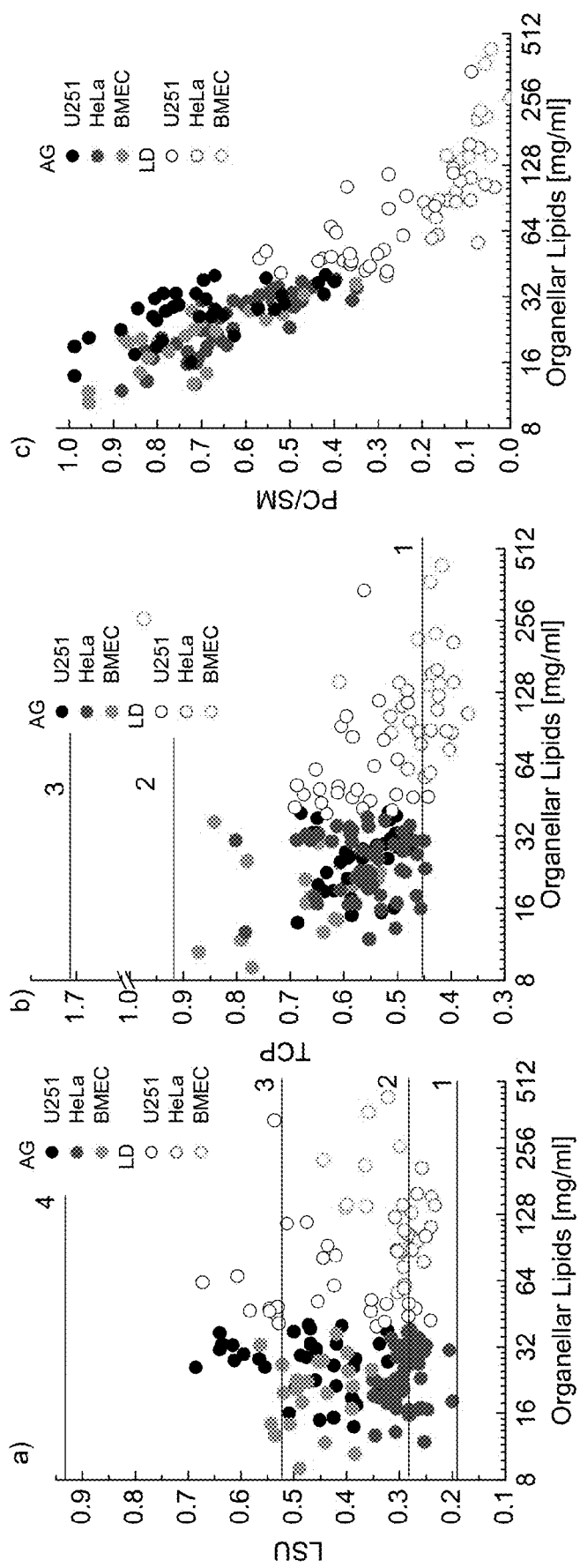
FIG. 11 shows organellar lipidome parameters LSU, TCP, PC/SM and lipid concentration of different cell lines. Concentration of organellar lipids vs. corresponding LSU (a) TCP (b), and PC/SM (c) of lipid constituents in AG (solid circles) and lipid droplets (open circles) for three cell lines—HeLa (red), U251 (human malignant glioblastoma cell line, black) and BMEC (human brain vascular endothelial cells, green). The standard error is comparable to the size of symbols. Abbreviations: AG—apparatus Golgi, ER—endoplasmic reticulum, mito—mitochondrion, LD—lipid droplets. As a reference, the levels of LSU shown by numbered horizontal lines in graph (a) correspond to: (1) Egg SM (16:0/18:1), (2) 16:1 SM (16:1/18:1), (3) OA (18:1). Levels of TCP shown by numbered horizontal lines in graph (b) correspond to: (1): GA (18:1E), LA (18:2E), (2) 16:1 SM (16:1E/18:1Z) (3) Egg SM (16:0/18:1Z). OA is oleic acid, LA is linoleic acid, Egg SM is chicken egg sphingomyelin, 16:1 SM is N-palmitoleoyl-D-erythro-sphingosylphosphorylcholine. Numbers in parenthesis show the number of carbon bonds (first) and the number of double bonds (second); letter after the second number denotes cis-(E) or trans-(Z) isomer of the double bond.

FIGS. 6 and 7 show some possible applications of lipidome analysis by BCA in cellular biology: heterogeneity of lipids in HeLa cell organelles (FIG. 10), heterogeneity of organellar lipid parameters in different cell cultures (FIG. 11).

Heterogeneity of Organellar Lipidomes in Cultured Cells.

Compartmentalization of biochemical processes suggests formation of different molecular environment in each type of cellular organelle. To gain insight into organelle-specific lipid content, lipidomes in ER, AG, mitochondria and LD in HeLa cells were compared. Consistent with different functions of these organelles in cellular metabolism, differences in the lipid composition were observed. A one-way analysis of variance shows that AG and LD contain at least 20% less of mono- and polyunsaturated lipids ($LSU_{AG}=0.29$) compared to that in ER ($LSU_{ER}=0.35$) and mitochondria ($LSU_{mito}=0.37$). This level of unsaturation is close to that of phospholipids with two chains of monounsaturated fatty acids (horizontal line 2 in FIG. 6). Also, LDs of HeLa cells contain less phospholipids with trans-C=C conformations ($TCP_{LD}=0.44$), than in other organelles ($TCP_{AG}=0.56$, $TCP_{ER}=0.58$, $TCP_{mito}=0.64$). This TCP parameter demonstrates that the trans-part of phospholipids in HeLa lipid droplets is close to zero. Besides, lipid droplets of HeLa cells contain more than 5 times less sphingolipids ($PC/SM_{LD}$=0.12) compared to others organelles ($PC/SM_{AG}$=0.63, $PC/SM_{ER}$=0.69, $PC/SM_{mito}$=0.70).

Interline Comparison of Organellar Lipidome.

Lipidome of two organelles, AG and LD, for three cell lines-HeLa, human malignant glioblastoma cells (U251) and human brain vascular endothelial cells (BMEC) were compared. Lipid droplets accumulation represents a biomarker of many cancers, and is specifically correlated with increased tumor progression in glioma. Herein, a method of the present disclosure, the composition of lipids in LDs with other organelles, such as AG, with the goal to obtain information on the dynamics between lipid trafficking inside live cells in real time can be compared. In all the cell lines measured, a difference between the saturation of lipids in Golgi apparatus as compared to other cellular sites was observed. As seen from FIG. 11, the number of unsaturated lipids in the AG membranes of HeLa cells (LSU=0.29), is more than 1.5 times lower than that in both BMEC (0.46) and U251 cell lines (0.50). The content of unsaturated phospholipids in lipid droplets is the same as that in AG of HeLa cells and, again, lower than that in lipid droplets for U251 (LSU=0.43) and BMEC (LSU=0.37). At the same time, the sphingolipids concentrations in AG of HeLa and U251 are very close (PC/SM 0.63 and 0.69), and slightly lower than that in AG of BMEC (0.73) (FIG. 11). The largest difference of sphingolipids content in all these three lines are found in lipid droplets. In the BMEC line, it is close to zero (0.06); in LD of the U251 cell line, this peak achieves 0.34, while HeLa sphingolipids in LD are in between (0.12) of that for BMEC and U251. This shows that our method is sensitive enough to differentiate the lipid profiles of organelles between different cells and cell lines.

The invention claimed is:

1. A method for determining a lipid composition in an organelle of a cell comprising a lipid component, the method comprising:
    determining the Raman spectrum of the organelle of the cell, wherein the cell is disposed on a substrate comprising:
        contacting the organelle of the cell with radiation having a wavelength of 400 nm to 1200 nm, wherein at least a portion of the radiation is scattered; and
        detecting the scattered radiation;
    optionally, determining a model Raman spectrum corresponding to the organelle of the cell; and
    comparing the Raman spectrum of the portion of the organelle with a model Raman spectrum, which does not include the lipid component, via biomolecular component analysis (BCA) wherein the difference between the Raman spectrum of the organelle of the cell and the model Raman spectrum correlates to the lipid composition in the organelle of the cell and the lipid composition in the organelle is quantitatively determined.

2. The method of claim 1, wherein the Raman spectrum of the organelle of the cell and the model Raman spectrum, or a residual Raman spectrum resulting from comparison of the Raman spectrum and the model Raman spectrum, comprise(s) wavelengths from 200 $cm^{-1}$ to 3200 $cm^{-1}$.

3. The method of claim 1, wherein the model Raman spectrum is a combination of two or more Raman spectra of cellular components other than lipid(s) and each Raman spectra is a Raman spectrum of a different cellular component.

4. The method of claim 3, wherein the two or more Raman spectra of cellular components other than lipid(s) are obtained from a database of Raman spectra of cellular components.

5. The method of claim 3, wherein the cellular components are chosen from proteins, RNA, DNA, polysaccharides, saccharides, and combinations thereof.

6. The method of claim 1, wherein in the comparison comprises minimizing a residual Raman spectrum resulting from comparison of the model Raman spectrum and Raman spectrum of the organelle of the cell.

7. The method of claim 6, wherein the comparison comprises adjusting the weighting of the two or more Raman spectra to minimize the residual Raman spectrum.

8. The method of claim 7, wherein the weighting is determined by mathematical fitting of the model Raman spectrum to the Raman spectrum of the organelle.

9. The method of claim 1, wherein relative amounts of saturated lipids to unsaturated lipids are determined.

10. The method of claim 1, wherein the organelle comprises unsaturated lipids and a degree of saturation of the unsaturated lipids is determined.

11. The method of claim 1, wherein, in the case where unsaturated lipids are present in the organelle, stereochemistry of the unsaturated lipids is determined.

12. The method of claim 1, wherein the organelle of the cell is from an isolated cell.

13. The method of claim 1, wherein the organelle of the cell is from a live or fixed cell.

14. The method of claim 1, wherein the method further comprises staining a cell to identify and/or select the organelle of the cell.

15. The method of claim 1, wherein the organelle of the cell has a volume of 1 cubic micron to 10 cubic microns.

16. The method of claim 1, wherein the radiation is laser radiation.

17. The method of claim 16, wherein the laser radiation has a wavelength of 488 nm, 532 nm, 632 nm, 785 nm, or 1064 nm.

18. The method of claim 1, wherein the organelle of the cell is from a cell disposed on a substrate.

19. The method of claim 1, further comprising diagnosing a disease in an individual.

20. The method of claim 1, wherein quantitative determination of the lipid composition in the organelle is lipid concentration, cholesterol concentration, phosphatidylcholine concentration, determination of trans- and cis-lipid isomer ratio, determination of lipid unsaturation level, or a combination thereof.

* * * * *